United States Patent
Kumar et al.

(10) Patent No.: US 12,430,386 B1
(45) Date of Patent: Sep. 30, 2025

(54) DATABASE PLAYBACK ARCHITECTURE FOR DISTRIBUTED WORKFLOW INTEGRATED APPLICATIONS

(71) Applicant: Express Scripts Strategic Development, Inc., St. Louis, MO (US)

(72) Inventors: Ghanshyam Kumar, Orlando, FL (US); Velchakravarthi Sadasivam, Leander, TX (US); Anithsen S. Larson, Lakeland, TN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 18/609,149

(22) Filed: Mar. 19, 2024

(51) Int. Cl.
G06F 16/81 (2019.01)
G16H 10/60 (2018.01)

(52) U.S. Cl.
CPC ............. G06F 16/81 (2019.01); G16H 10/60 (2018.01)

(58) Field of Classification Search
CPC ................................ G06F 16/81; G16H 10/60
USPC .................. 707/602, 694, 755, 802, 803
See application file for complete search history.

(56) References Cited

U.S. PATENT DOCUMENTS

| | | | |
|---|---|---|---|
| 7,403,948 B2 | 7/2008 | Ghoneimy | |
| 7,953,580 B2 | 5/2011 | Cleary | |
| 8,275,720 B2 | 9/2012 | Islam | |
| 10,496,793 B1* | 12/2019 | Lawrence | ............... G16H 40/20 |
| 10,775,976 B1* | 9/2020 | Abdul-Jawad | ............ G06F 9/54 |
| 2003/0074244 A1 | 4/2003 | Braxton | |
| 2003/0187763 A1 | 10/2003 | Jordan | |
| 2005/0216881 A1 | 9/2005 | Sankaran | |
| 2006/0195817 A1 | 8/2006 | Moon | |
| 2006/0206352 A1 | 9/2006 | Pulianda | |
| 2007/0250335 A1 | 10/2007 | Hodges | |
| 2008/0040455 A1 | 2/2008 | MacLeod | |
| 2008/0162500 A1 | 7/2008 | Dettinger | |
| 2011/0137702 A1 | 6/2011 | Hodges | |
| 2012/0150751 A1 | 6/2012 | Pandey | |
| 2012/0246122 A1* | 9/2012 | Short | ...................... G06F 16/20 707/694 |
| 2012/0296687 A1 | 11/2012 | Satyanarayana | |
| 2016/0364211 A1* | 12/2016 | Chau | ......................... G06F 8/20 |

(Continued)

OTHER PUBLICATIONS

Wikipedia, Playback Singer, https://en.wikipedia.org/wiki/Playback_singer, accessed as early as Oct. 3, 2023.

*Primary Examiner* — Phong H Nguyen
(74) *Attorney, Agent, or Firm* — Harness IP

(57) ABSTRACT

A computer system includes multiple data sources each configured to store different data for a portion of a distributed workflow integrated application, a data modeling engine, and processor hardware configured to execute instructions to define a standard data model, the standard data model configured to support a workflow, obtain access details for obtaining data from the multiple data sources, set up the data modeling engine to connect to the multiple data sources, based on the obtained access details, prepare a configuration table to return a list of the multiple data sources used in the workflow and an execution order of the multiple data sources, collect, by the data modeling engine, data from the multiple data sources, and prepare a data object using the standard data model and the data collected from the multiple data sources.

18 Claims, 10 Drawing Sheets

(56) References Cited

U.S. PATENT DOCUMENTS

2023/0350862 A1* 11/2023 Munuri ................ G06F 16/258
2023/0394233 A1* 12/2023 Lequeux ............... G06F 40/205

* cited by examiner

DATABASE PLAYBACK ARCHITECTURE FOR DISTRIBUTED WORKFLOW INTEGRATED APPLICATIONS

FIELD

The present disclosure relates to a database playback architecture for distributed workflow integrated applications.

BACKGROUND

In a complex and distributed workflow based integrated application, interactions occur between multiple systems and data sources to obtain data needed to support process execution. Data collection may happen at different stages, which may be the backbone of the workflow execution. If data is missing, or the data source is unavailable at a certain time, the workflow may stop. Therefore, data collection may impact performance.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

An example computer system includes multiple data sources each configured to store different data for a portion of a distributed workflow integrated application, a data modeling engine, and processor hardware configured to execute instructions to define a standard data model, the standard data model configured to support a workflow, obtain access details for obtaining data from the multiple data sources, set up the data modeling engine to connect to the multiple data sources, based on the obtained access details, prepare a configuration table to return a list of the multiple data sources used in the workflow and an execution order of the multiple data sources, collect, by the data modeling engine, data from the multiple data sources, and prepare a data object using the standard data model and the data collected from the multiple data sources.

In some examples, the processor hardware is configured to execute instructions to build, by the data modeling engine, the workflow for the distributed workflow integrated application, and integrate the data object with the workflow built by the data modeling engine.

In some examples, the data object is an extensible markup language (XML) data object or a JavaScript object notation (JSON) data object. In some examples, the processor hardware is configured to execute instructions to identify at least one dependency among the multiple data sources, and define the execution order of the multiple data sources based on at least one dependency.

In some examples, obtaining access details for obtaining data from the multiple data sources includes obtaining multiple application programming interfaces each corresponding to a different one of the multiple data sources, and collecting data from the multiple data sources includes the data modeling engine accessing the multiple data sources via the multiple application programming interfaces.

In some examples, the processor hardware is configured to execute instructions to assign a first one of the multiple data sources as a mandatory data source in the workflow, and assign a second one of the multiple data sources as an optional data source in the workflow.

In some examples, the processor hardware is configured to execute instructions to identify an outbound process based on the workflow and at least one attribute, and generate an outbound event in response to identification of the outbound process.

In some examples, the multiple data sources include at least three different data sources each configured to store different data corresponding to different portions of portion of the distributed workflow integrated application.

In some examples, the data object includes multiple tables, at least one of the multiple tables is configured to store healthcare patient data, and at least one of the multiple tables is configured to store healthcare claims data.

In some examples, the standard data model includes at least one of a pharmacy level rule, a patient identification check rule, a routing rule, a medical rule, a duplicate rule, an eligibility prioritization rule, and a configurable sequencing rule.

An example method for database playback for distributed workflow integrated applications includes defining a standard data model, the standard data model configured to support a workflow, obtaining access details for obtaining data from multiple data sources, the multiple data sources each configured to store different data for a portion of a distributed workflow integrated application, setting up a data modeling engine to connect to the multiple data sources, based on the obtained access details, preparing a configuration table to return a list of the multiple data sources used in the workflow and an execution order of the multiple data sources, collecting, by the data modeling engine, data from the multiple data sources, and preparing a data object using the standard data model and the data collected from the multiple data sources.

In some examples, the method includes building, by the data modeling engine, the workflow for the distributed workflow integrated application, and integrating the data object with the workflow built by the data modeling engine.

In some examples, the data object is an extensible markup language (XML) data object or a JavaScript object notation (JSON) data object. In some examples, the method includes identifying at least one dependency among the multiple data sources, and defining the execution order of the multiple data sources based on at least one dependency.

In some examples, obtaining access details for obtaining data from the multiple data sources includes obtaining multiple application programming interfaces each corresponding to a different one of the multiple data sources, and collecting data from the multiple data sources includes the data modeling engine accessing the multiple data sources via the multiple application programming interfaces.

In some examples, the method includes assigning a first one of the multiple data sources as a mandatory data source in the workflow, and assigning a second one of the multiple data sources as an optional data source in the workflow.

In some examples, the method includes identifying an outbound process based on the workflow and at least one attribute, and generating an outbound event in response to identification of the outbound process.

In some examples, the multiple data sources include at least three different data sources each configured to store different data corresponding to different portions of portion of the distributed workflow integrated application.

In some examples, the data object includes multiple tables, at least one of the multiple tables is configured to store healthcare patient data, and at least one of the multiple tables is configured to store healthcare claims data.

In some examples, the standard data model includes at least one of a pharmacy level rule, a patient identification check rule, a routing rule, a medical rule, a duplicate rule, an eligibility prioritization rule, and a configurable sequencing rule.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

High-Volume Pharmacy

Figure 1:
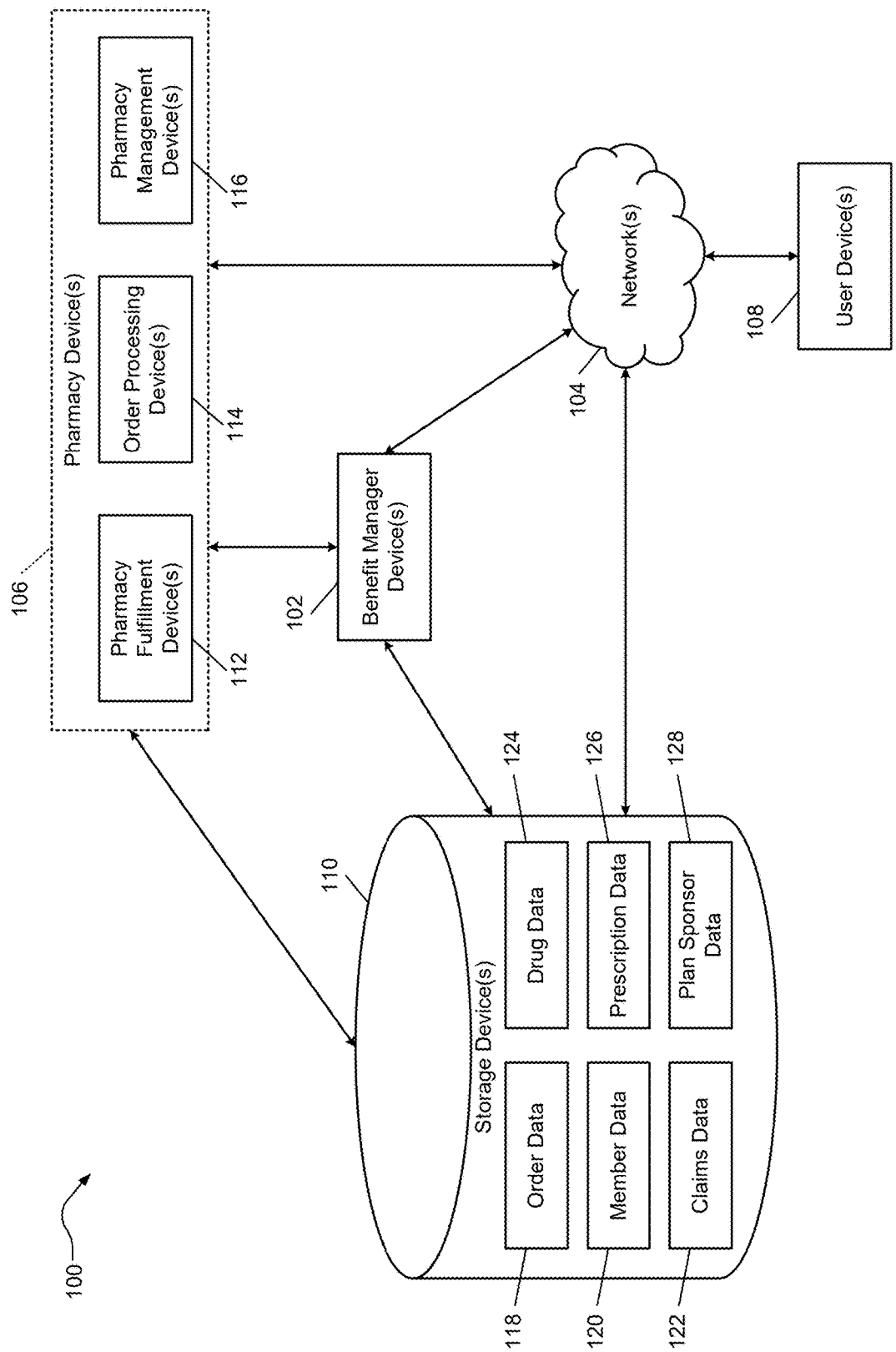
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug is successfully adjudicated. The aforementioned adjudication operations generally occur before the copayment is received and the prescription drug is dispensed. However, in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally, or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
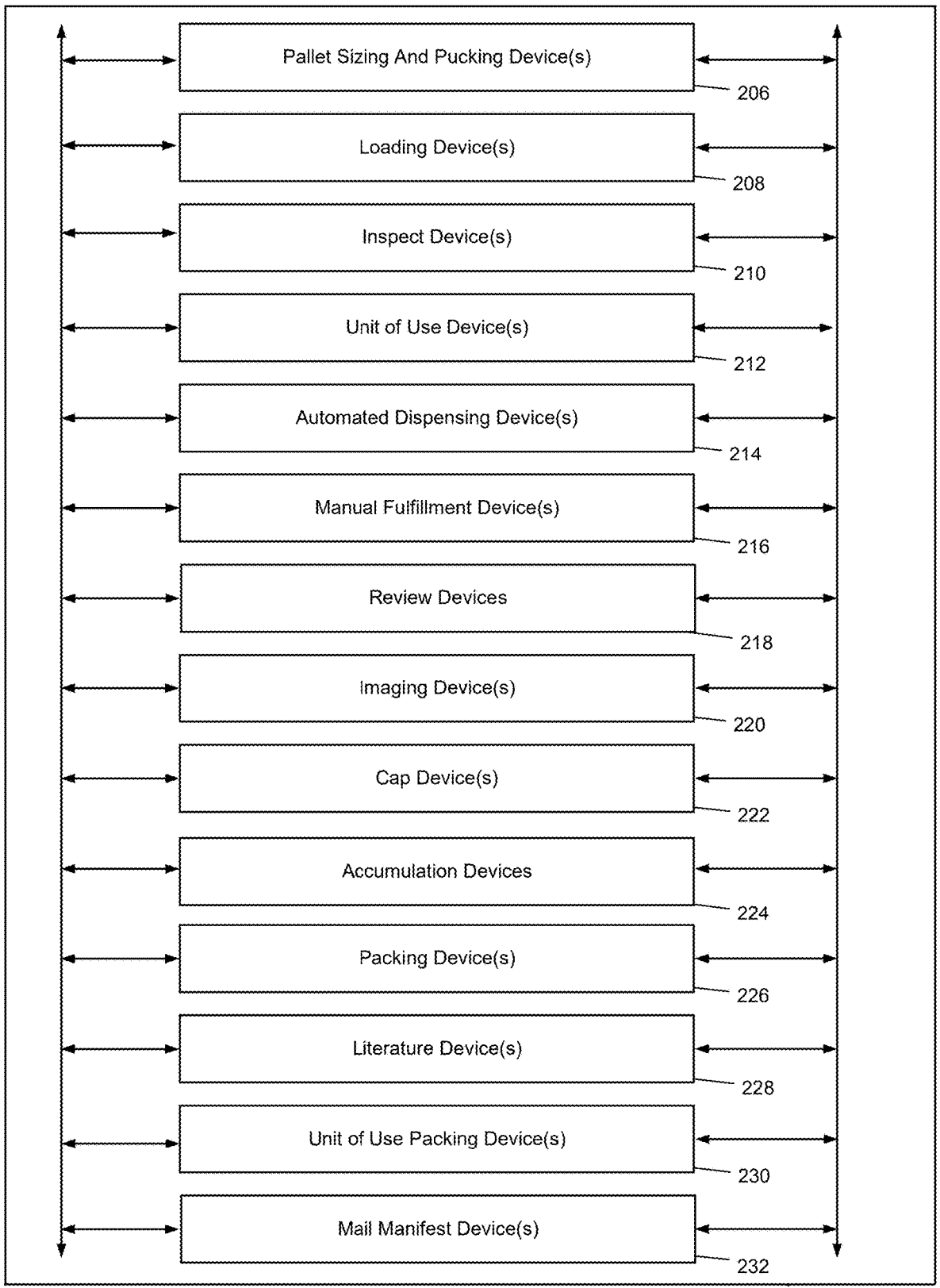
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
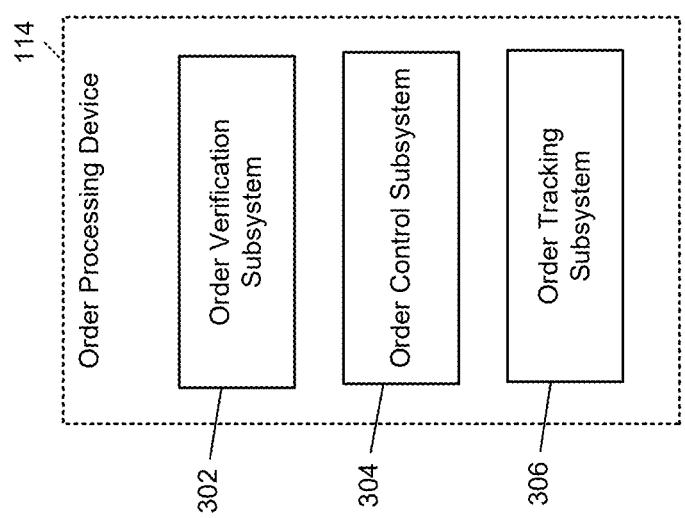
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Database Playback Architecture for Distributed Workflow Integrated Applications

In a complex and distributed workflow based integrated application, interactions occur between multiple systems and data sources to obtain data needed to support process execution. Data collection may happen at different stages, which may be the backbone of the workflow execution. If data is missing, or the data source is unavailable at a certain time, the workflow may stop. Therefore, data collection may impact performance.

In some examples, different application programming interfaces (APIs) are called at different stages of the workflow, based on data needs. This makes the process dependent on the data source configuration in the workflow, and may need further changes when there are changes id data attributes (e.g., for other consumers).

In some example embodiments described herein, playback signing (e.g., a database playback architecture) for a workflow based implementation may make the workflow independent of the data sources, more streamlined, have increased scalability, and be configurable irrespective of the data. A data modeling engine may be configured to collect data from multiple sources, and build a standard data model to support workflow execution. The data model preparation may occur before starting the workflow.

Figure 4:
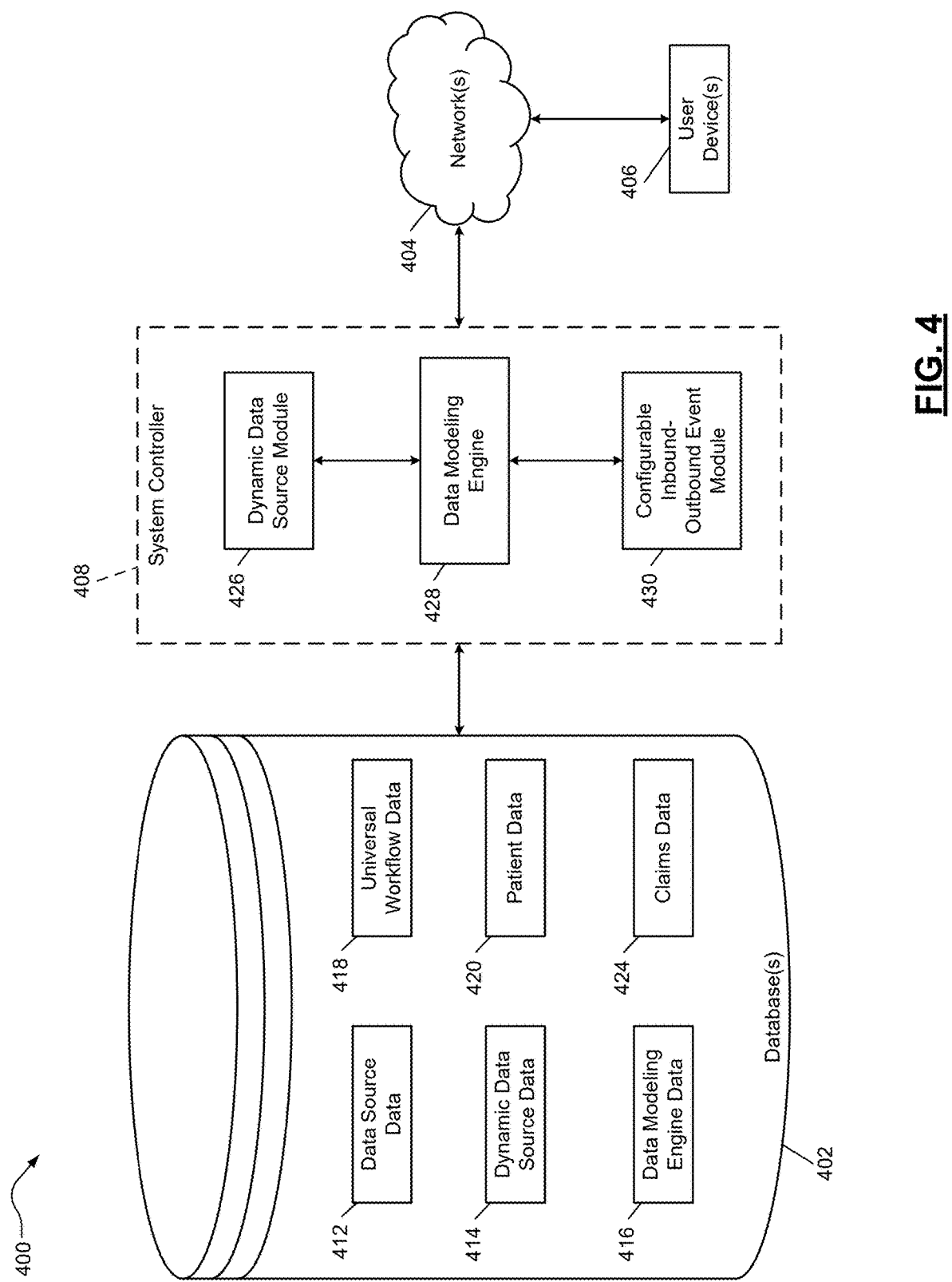
FIG. 4 is a functional block diagram of an example system for database playback for distributed workflow integrated applications.

FIG. 4 is a functional block diagram of an example system 400 for database playback architecture for distributed workflow integrated applications, which includes one or more databases 402. While the system 400 is generally described as being deployed in a computer network system, the database 402 and/or components of the system 400 may otherwise be deployed (for example, as a standalone computer setup). The system 400 may include a desktop computer, a laptop computer, a tablet, a smartphone, etc.

As shown in FIG. 4, the database 402 stores data source data 412, dynamic data source data 414, data modeling engine data 416, universal workflow data 418, patient data 420, and claims data 424. In various implementations, the database 402 may store other types of data as well, or may not store all of the example data types illustrated in FIG. 4.

The data source data 412, dynamic data source data 414, data modeling engine data 416, universal workflow data 418, patient data 420, and claims data 424 may be located in different physical memories within the database 402, such as different random access memory (RAM), read-only memory (ROM), a non-volatile hard disk or flash memory, etc., or be spread across multiple different databases. In some implementations, the data source data 412, dynamic data source data 414, data modeling engine data 416, universal workflow data 418, patient data 420, and claims data 424 may be located in the same memory (such as in different address ranges of the same memory). In various implementations, the data source data 412, dynamic data source data 414, data modeling engine data 416, universal workflow data 418, patient data 420, and claims data 424 may each be stored as structured or unstructured data in any suitable type of data store.

As shown in FIG. 4, a system controller 408 may include one or more modules, including a dynamic data source module 426, a data modeling engine 428, and a configurable inbound-outbound event module 430. These example modules are provided for purposes of illustration, and other embodiments may include more or less modules, functions of different software features implemented in other modules or controller locations, more than one system controller, more than one database, data distributed to other databases, etc.

In various implementations, a system developer may access the system controller 408 via the user device 406. The user device 406 may include any suitable user device for displaying text and receiving input from a user, including a desktop computer, a laptop computer, a tablet, a smartphone, etc. In various implementations, the user device 406 may access the database 402 or the system controller 408 directly, or may access the database 402 or the system controller 408 through one or more networks 404. Example networks may include a wireless network, a local area network (LAN), the Internet, a cellular network, etc.

In some examples, the data source 412 may include data stored in one or more data sources accessed by an application, which may be stored in multiple different databases, cloud storage locations, structured data tables, etc. The dynamic data source data 414 may include data for storing copies, transformations, etc. of data from the data sources, for storage in a dynamic data source used in a database playback architecture for distributed workflow integrated applications.

The data modelling engine data 416 and the universal workflow data 418 may include any suitable data for execution by the data modeling engine 428, which may interact with the dynamic data source module 426 to generate a dynamic data source (e.g., by copying data from other data sources used by one or more applications, etc.). The patient data 420 and claims data 424 may include any suitable patent and claims healthcare data, which may be stored in the data sources, processed by healthcare applications, etc. For example, the configurable inbound-outbound event module 430 may be configured to work with the dynamic data source module 426 and the data modeling engine 428 to provide responses to requests (e.g., user or system requests) from healthcare processing applications, etc.

Figure 5:
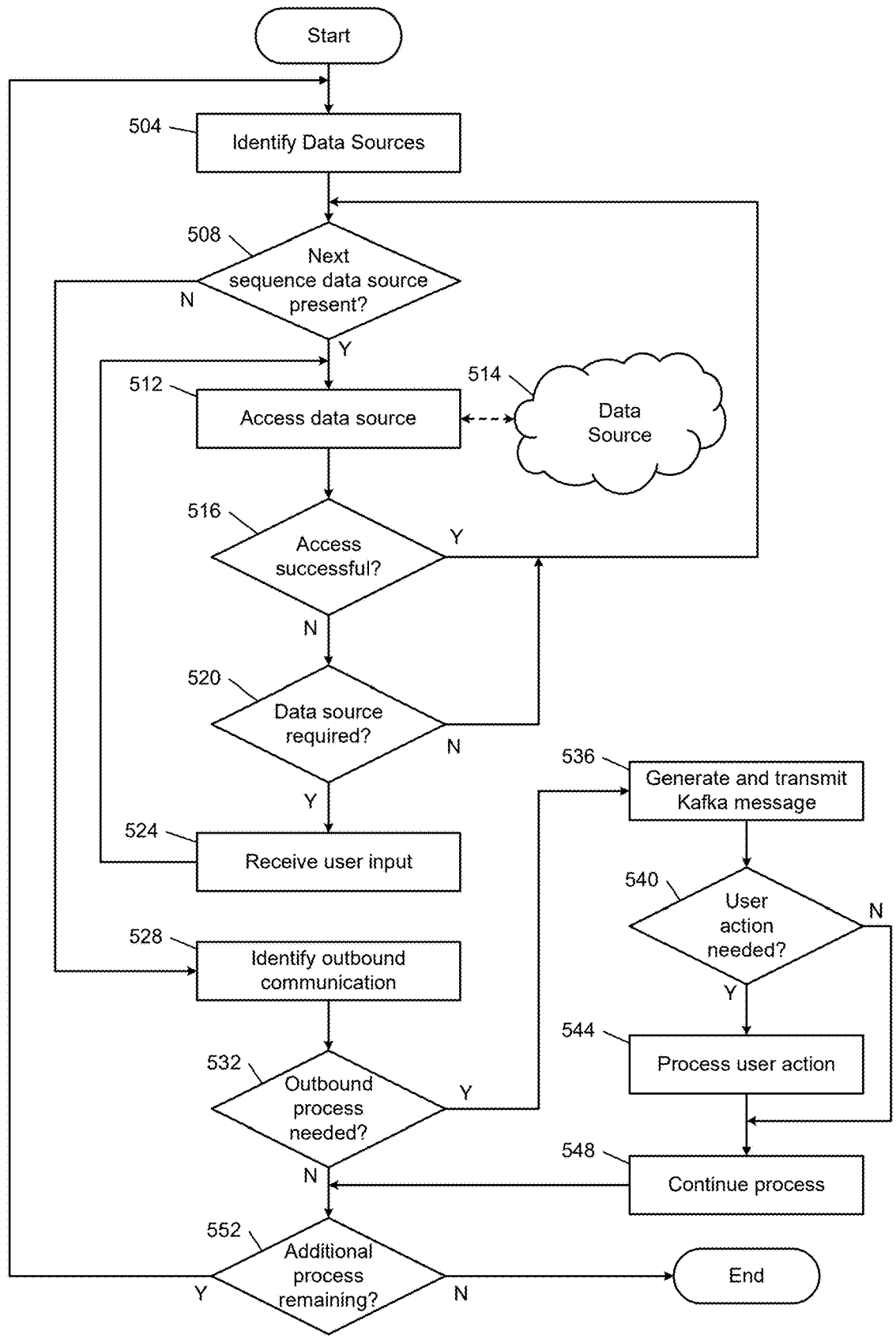
FIG. 5 is a flowchart depicting an example process for executing database playback for distributed workflow integrated applications.

FIG. 5 is a flowchart depicting an example process for a database accessing data sources via distributed workflow integrated applications. In various implementations, the process of FIG. 5 may be executed by the system controller 408.

At 504, the process begins by identifying data sources, such as identifying data sources needed by a process to access data during execution of the process (e.g., data sources the process calls to for obtaining data). At 508, control determines whether a next (or first) data source in the sequence of data sources used in the process is present. If so, control accesses the data source 514 at 512, such as by making an API call to a patient database, a cloud server storage system, etc.

At 516, control determines whether the data source 514 was accessed successfully. If so, control returns to 508 to determine whether any additional data sources remain in the sequence of data sources of the process. If access to the data source 514 is not successful at 516, control proceeds to 520 to determine whether the data source 514 is required by the process. If not, control returns to 508 to determine whether any additional data sources remain in the sequence of data sources of the process.

If control determines at 520 that the data source 514 is required, control proceeds to 524 to receive user input. The user input may be, for example, a request to process a specific record, claim, patient event, etc. Control then returns to 508 to determine whether any additional data sources remain in the sequence of data sources of the process.

Once all data sources have been processed at 508, control proceeds to 528 to identify an outbound communication. For example, the output communication may be a message transmitted by the process. At 532 control determines whether an outbound process is needed. Outbound processes may be associated with, for example, an API, a message, a queue, a Topic/Kafka, a database, desktop automation, etc.

If control determines at 532 that an outbound process is needed, control proceeds to 536 to generate and transmit a message (e.g., a Kafka message), or other suitable outbound communication or request. At 540, control determines whether a user action is needed. If not, control continues the process at 548. If a user action is needed, control processes the user action at 544. At 552, control determines whether any additional processes are remaining. If so, control returns to 504 to identify data sources for the next process. If no additional processes remain at 552, the process may end.

Figure 6:
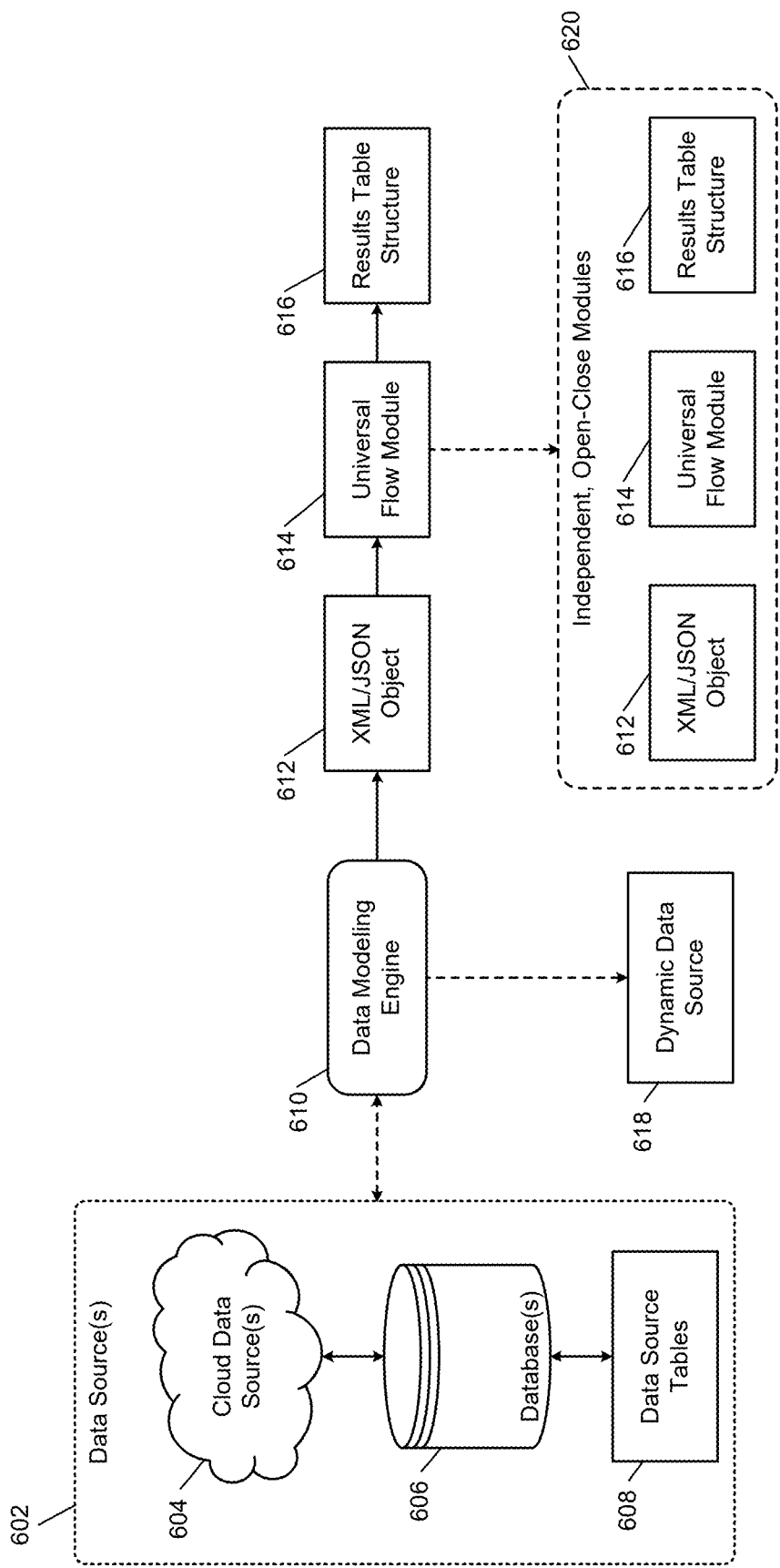
FIG. 6 is a functional block diagram illustrating example components of the system of FIG. 4.

FIG. 6 is a functional block diagram illustrating example components of the system of FIG. 4. As shown in FIG. 6, the data sources 602 include one or more cloud data sources 604, one or more database 606, one or more data source tables 608, etc.

A data modeling engine 610 is in communication with the data sources 602. The data modeling engine 610 is configured to obtain data from the data sources 602 for storage in a dynamic data source 618. In some examples, the data modeling engine 610 may be configured to generate an XML/JSON object 612, a universal workflow module 614, and a results table structure 616. This may result in independent, open-close modules 620, such as the XML/JSON object 622, the universal flow module 624, and the results table structure 626 (e.g., which may be similar or identical to the XML/JSON object 612, the universal workflow module 614, and the results table structure 616).

As described above, creating a workflow which is dependent on a data source may cause slowness or execution failure at different stages of the process, due to unavailability of data, a slow response from integrated data sources, etc. In various implementations, if the data is not changing frequently, or if the workflow may be processed quickly, all data sources may be invoked at a beginning of the process to collect necessary information for supporting a workflow.

For example, a database playback architecture for distributed workflow integrated applications may include multiple layers, where a first layer is configured to collect data to develop a foundation (e.g., a data object such as a ghost model) for the workflow. A core engine may collect data from different data sources, and filter out necessary information for executing an application or workflow (e.g., determining which data may be accessed or requested by the application or workflow).

After collecting data from different sources, the collected data may be stored in its own model. This may make the process more flexible for different consumers to filter out necessary information, and keep the filtered out information ready for data stitching.

A second layer may be configured to create a common data structure for a workflow. The common data structure may be based on, for example, data collected from different sources, and needs of a consumer. Different attributes may be combined in a standard data model to make a data object ready for a workflow.

In various implementations, the process may be scalable, where collecting data from different data sources is configurable. A configurable data source may make the process configurable for any consumers of the workflow. A common data model (e.g., a ghost model, where the workflow does not know who and what is driving the process) may be independent, because the workflow may execute on a common data model irrespective of the data sources (which may make the workflow streamlined and independent of the data sources). For example, a ghost data model engine may be configured to collect data from different sources, and prepare a common data model.

Figure 7:
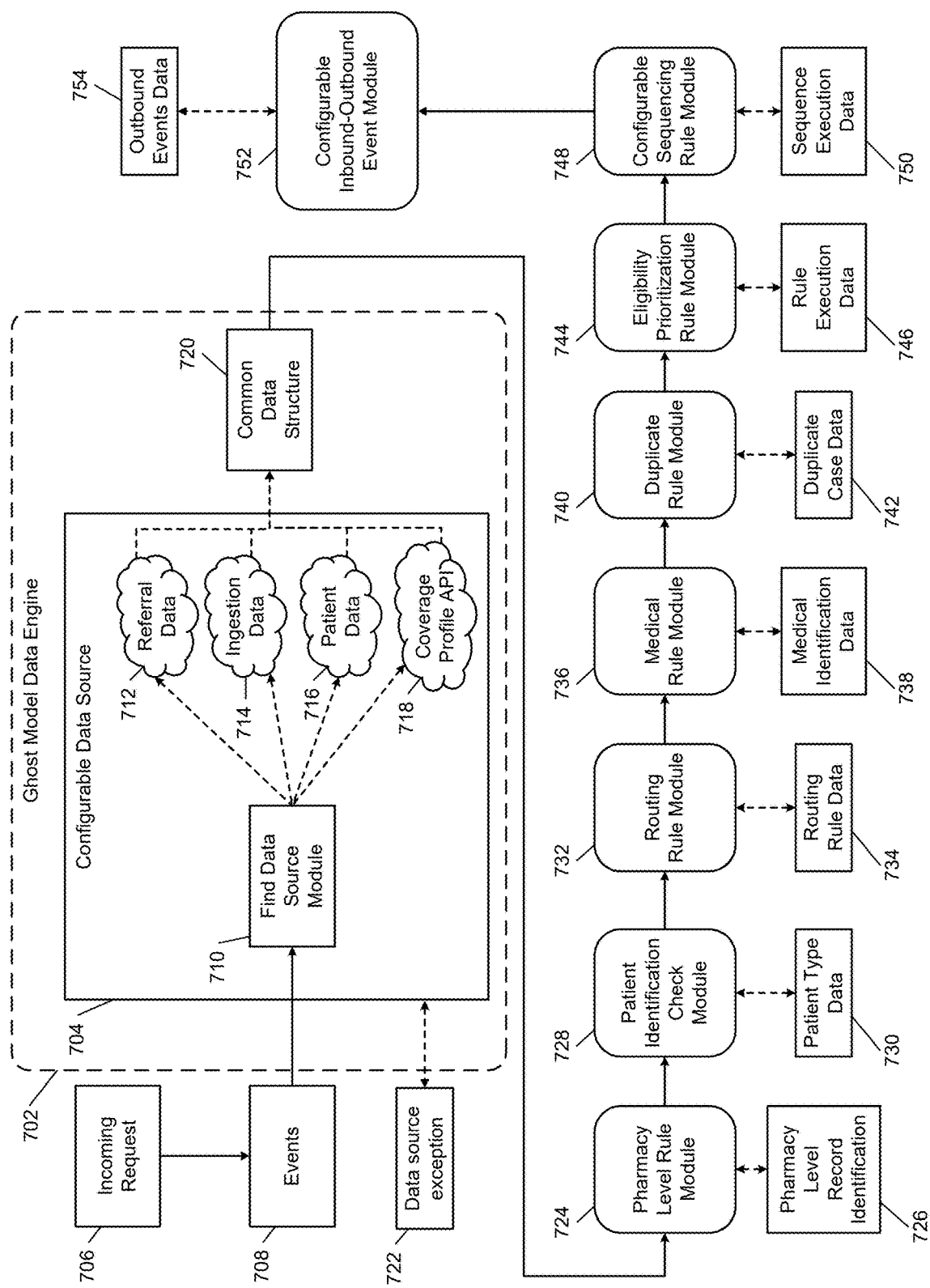
FIG. 7 is a functional block diagram of an example model data engine and multiple data sources.

FIG. 7 is a functional block diagram of an example model data engine and multiple data sources. As shown in FIG. 7, a ghost model data engine 702 receives events 708, which may be generated in response to incoming requests 706.

For example, the ghost model data engine 702 may include a configurable data source 704, which includes a find data source module that receives the events 708. The find data source module 710 may be connected with multiple data sources, such as a referral data source 712, an ingestion data source 714, a patient data source 716, and a coverage profile API data source 718. In some examples, the configurable data source 704 may implement runtime execution of application programming interfaces (APIs) to obtain data for case processing. The sources of data may be different depending on the process/event type.

The configurable data source 704 may be configured to access data source exceptions 722. As shown in FIG. 7, the ghost model data engine 72 may be configured to generate a common data structure 720, based on, for example, the referral data source 712, the ingestion data source 714, the patient data source 716, and the coverage profile API data source 718. The data sources illustrated in FIG. 7 are for purposes of example illustration, and other example embodiments may include more or less (or other) suitable data sources.

The common data structure 720 may include multiple different rules, modules, data types, etc. For example, as shown in FIG. 7, a pharmacy level rule module 724 is configured to access pharmacy level record identification data 726 (e.g., to support any other pharmacy), a patient identification check module 728 is configured to access patient type data 730, and a routing rule module 732 is configured to access routing rule data 734.

A medical rule module 736 is configured to access medical identification data 738, a duplicate rule module 740 is configured to access duplicate case data 742, an eligibility prioritization rule module 744 is configured to access rule exclusion data 746 (e.g., for consideration of eligibility out of multiple cart finder and ESI results), and a configurable sequencing rule module 748 is configured to access sequence execution data 750 (e.g., to correct a payer sequence based on a configurable rule engine). The modules and data illustrated in FIG. 7 are for purposes of example illustration, and other example embodiments may include more or less (or other) suitable modules, data types, etc.

A configurable inbound-outbound event module 752 is configured to generate outbound events data 754. For example, the configurable inbound-outbound event module 752 may be configured to identify outbound events based on the process and attributes, to simplify the process and make it more flexible for any changes for new process onboarding.

Figure 8:
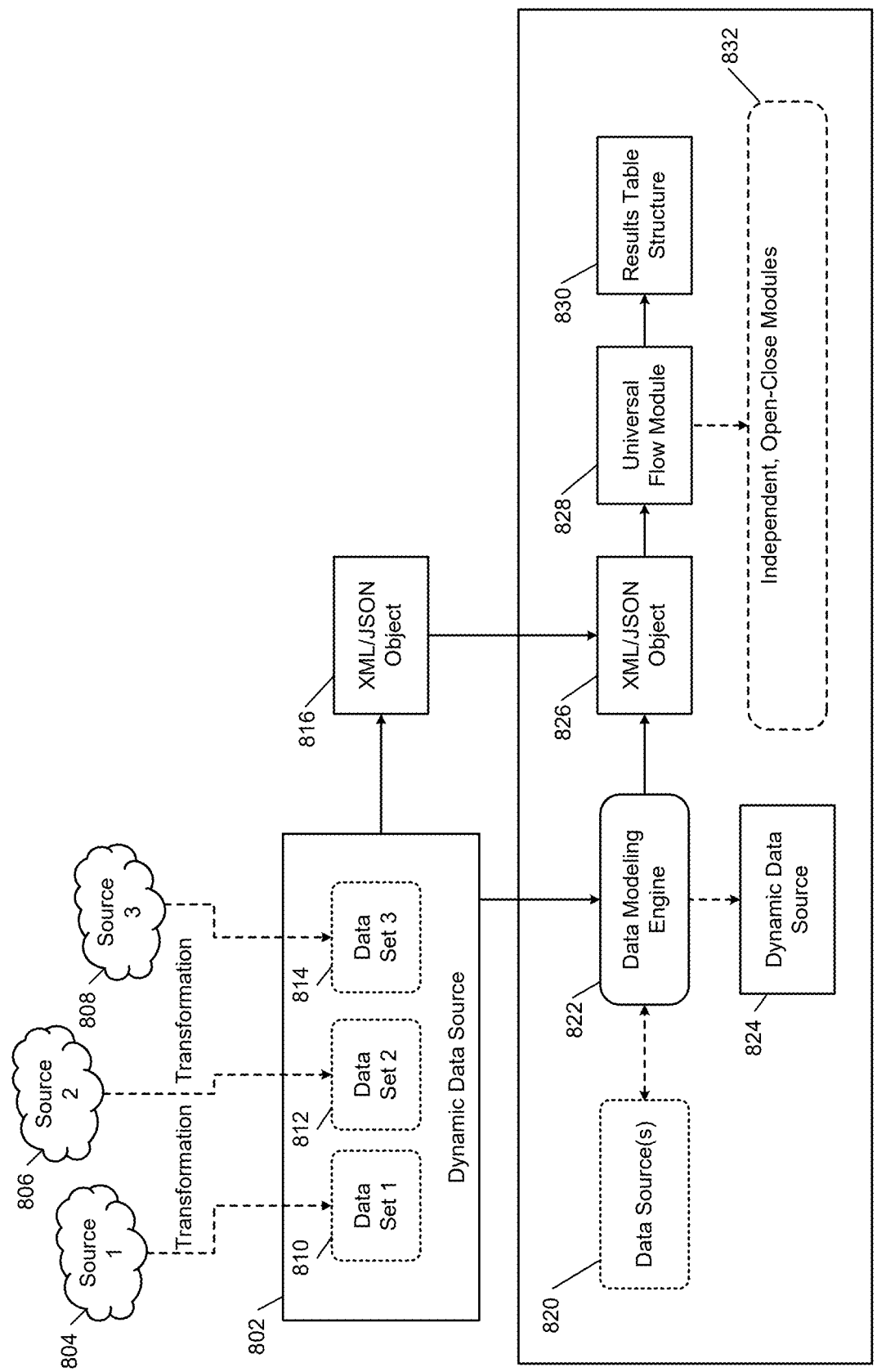
FIG. 8 is a functional block diagram of an example process for transforming multiple data sources into a dynamic data source using a data modeling engine.

FIG. 8 is a functional block diagram of an example process for transforming multiple data sources into a dynamic data source using a data modeling engine. For example, FIG. 8 may be considered as illustrating a transformation of the method for accessing data sources during a process execution as shown in FIG. 5, into the dynamic data source and workflow generated by the data modelling engine as shown in FIG. 6.

As shown in FIG. 8, a dynamic data source 802 includes a first data set 810 corresponding to a first data source 804, a second data set 812 corresponding to a second data source 806, and a third data set 814 corresponding to a third data source 808. The dynamic data source 802 may be generated by a data modelling engine 822. For example, the data sources 820 may include the first data source 804, the second data source 806 and the third data source 808, and the dynamic data source 824 may include the dynamic data source 802.

The dynamic data source 802 may be used to create an XML/JSON object 816 (e.g., by the data modeling engine 822), and the XML/JSON object 826 may include the XML/JSON object 816. As shown in FIG. 8, the data modelling engine 822 may be configured to generate a universal workflow module 828 and a results table structure 830, which may be developed as independent open-close modules 832.

Figure 9:
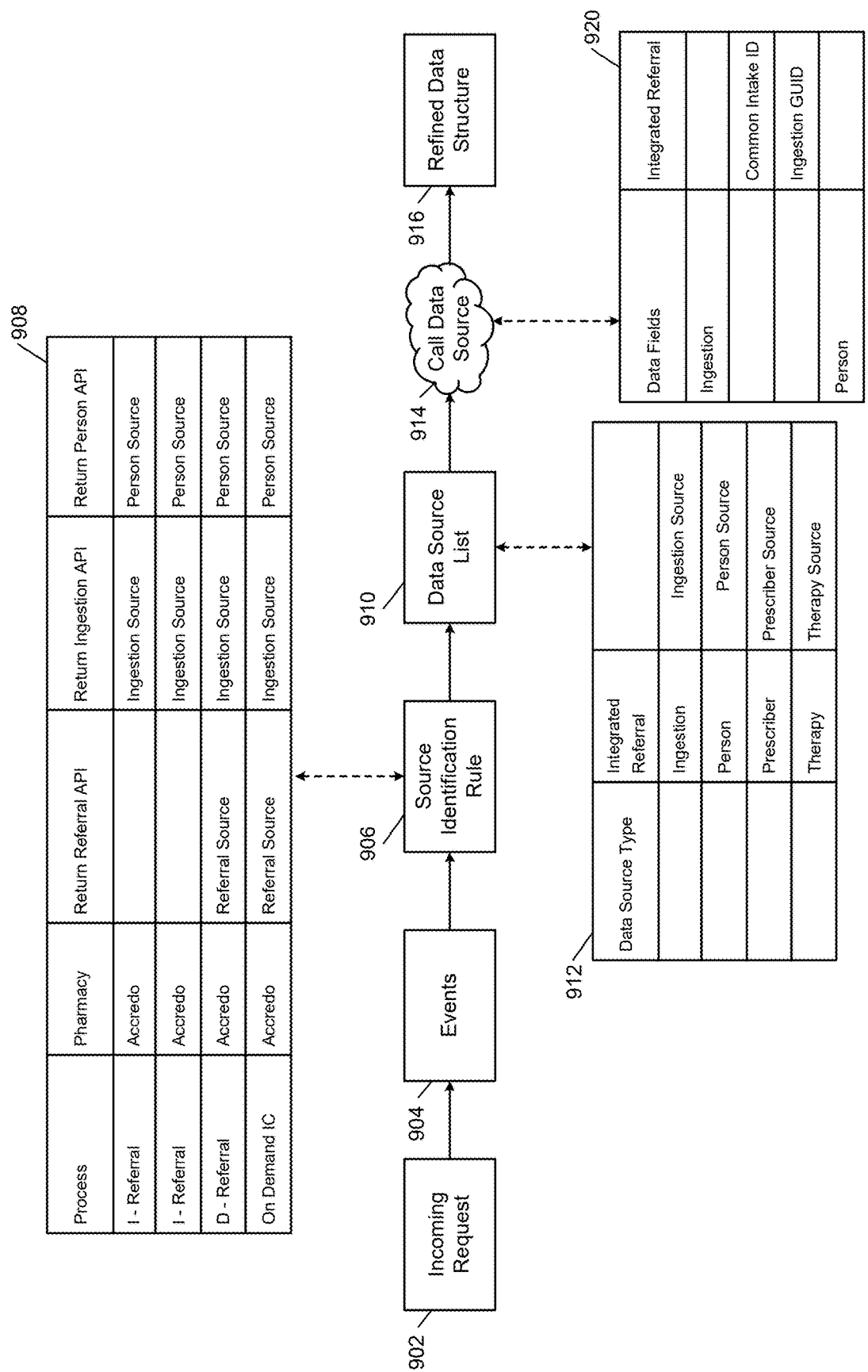
FIG. 9 is a functional block diagram illustrating example data sources and table data structures.

FIG. 9 is a functional block diagram illustrating example data sources and table data structures. As shown in FIG. 9, an incoming request 902 (e.g., from a user or system application) may generate one or more events 904, which correspond to a source identification rule 906.

FIG. 9 illustrates an example source identification rule table 908, which includes multiple example column and row values, although other example embodiments may include more or less rows and columns, other data types and values, etc. For example, the source identification rule table 908 may include a 'Process' column (e.g., to identify a type of referral, on demand, etc.), a 'Pharmacy' column, a 'Return Referral API' column designating a referral source, a 'Return Ingestion API' column designating an ingestion source, and a 'Return Person API' column identifying a person source.

A data source list 910 includes a data source list table 912, which includes multiple example column and row values, although other example embodiments may include more or less rows and columns, other data types and values, etc. For example, the data source list table 912 may include a 'Data Source Type' column, an 'Integrated Referral' column (e.g., indicating whether the referral came from ingestion, a person, a prescriber, therapy, etc.), and another column indicating ingestion source, person source, prescriber source, therapy source, etc.

A call data source module 914 may access a data source table 920, which includes multiple example column and row values, although other example embodiments may include more or less rows and columns, other data types and values, etc. For example, the data source table 920 may include a 'Data Fields' column (e.g., identifying ingestion fields, a person field, etc.), and an 'Integrated Referral' column (e.g., identifying a common intake identifier, an ingestion GUID, etc.). The output of the various modules may be stored in a refined data structure 916.

Database Playback Architecture Processes

Figure 10:
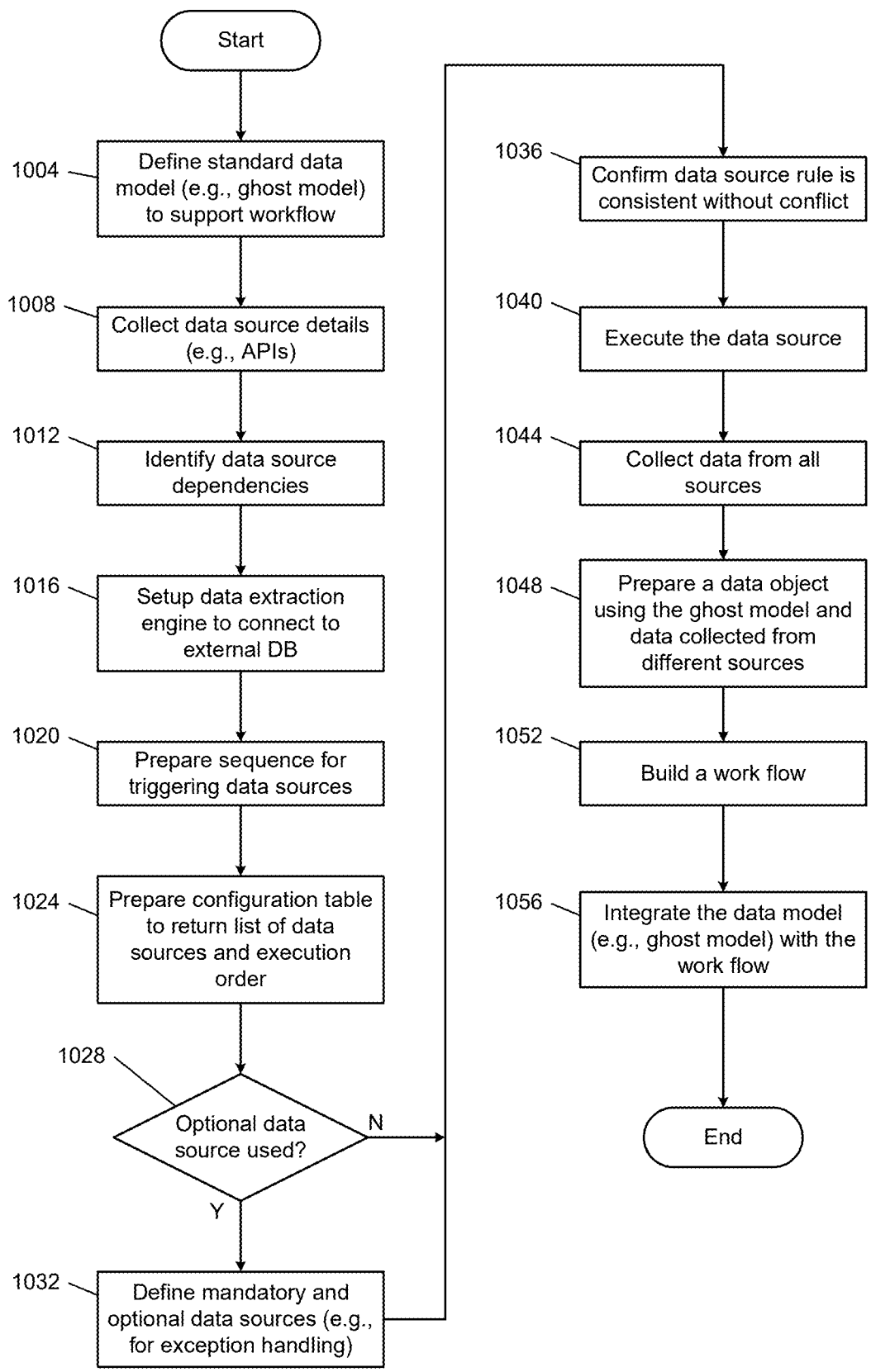
FIG. 10 is a flowchart depicting an example process for building a dynamic data source and integrating a data model with a workflow.

FIG. 10 is a flowchart depicting an example process for building a dynamic data source and integrating a data model with a workflow. In various implementations, the process of FIG. 10 may be executed by the system controller 408, such as the dynamic data source module 426, the data modeling engine 428, and/or the configurable inbound-outbound event module 430.

At 1004, the process begins by defining a standard data model (e.g., a ghost model), to support a workflow. Control then collects data source details (e.g., application programming interfaces for each data source), at 1008.

At 1012, the process identifies data source dependencies, and then sets up a data extraction engine to connect to an external database at 1016. Control prepares a sequence for triggering the data sources at 1020, and prepares a configuration table to return a list of data sources, and an execution order, at 1024.

Control is configured to determine at 1028 whether an optional data source will be used. If so, control proceeds to 1032 to define which data sources are mandatory and which are optional (e.g., for exception handling). After defining the mandatory and optional data sources at 1032, or determining that optional and mandatory data sources will not be defined at 1028, control proceeds to 1036 to confirm that a data source rule is consistent without conflict.

If the data source rule is consistent without conflict at 1036, control proceeds to execute the data source at 1040. Control then collects data from all data sources at 1044, and prepares a data object using the ghost model and data collected from the different data sources, at 1048. At 1052 control builds a workflow, and the data model (e.g., ghost model) is integrated with the workflow at 1056.

Example embodiments may be implemented using any suitable database technical components, such as Pega for a dynamic data source using decision tables, and a standard data model using data transformation and an integration rule to build a backend XML, an Oracle database, an extensible markup language (XML) data structure, representational state transfer (REST) APIs, etc. In other examples, the architecture may be implemented using any Java, Camunda, other business process management (BPM) tools, etc., which may support calling an API/web services/messages/Kafka, making data sources configurable, building a data structure in any standard format (such as XML or JSON), etc.

In case of any exception during data source execution, various implementations may use any suitable method of retry, exception handling, routing for manual review and process restart if other approaches are not successful, etc. If a failure occurs in the workflow, a similar dynamic model may be used to execute necessary data sources before starting a next step. Example architectures may be flexible for a complete workflow, as well as for small modules which can be integrated as a black box based on using the output of one model as an input for a next model.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system comprising:
multiple data sources each configured to store different data for a portion of a distributed workflow integrated application;
a data modeling engine; and
processor hardware configured to execute instructions to
define a standard data model, the standard data model configured to support a workflow,
obtain access details for obtaining data from the multiple data sources,
set up the data modeling engine to connect to the multiple data sources, based on the obtained access details,
prepare a configuration table to return a list of the multiple data sources used in the workflow and an execution order of the multiple data sources,
collect, by the data modeling engine, data from the multiple data sources, and
prepare a data object using the standard data model and the data collected from the multiple data sources;
build, by the data modeling engine, the workflow for the distributed workflow integrated application, using a dynamic data source with decision tables; and
integrate the data object with the workflow built by the data modeling engine using at least one of an extensible markup language (XML) data structure or a representational state transfer (REST) application programming interface (API).

2. The computer system of claim 1, wherein the data object is an extensible markup language (XML) data object or a JavaScript object notation (JSON) data object.

3. The computer system of claim 1, wherein the processor hardware is configured to execute instructions to:
identify at least one dependency among the multiple data sources; and
define the execution order of the multiple data sources based on at least one dependency.

4. The computer system of claim 1, wherein:
obtaining access details for obtaining data from the multiple data sources includes obtaining multiple application programming interfaces each corresponding to a different one of the multiple data sources; and
collecting data from the multiple data sources includes the data modeling engine accessing the multiple data sources via the multiple application programming interfaces.

5. The computer system of claim 1, wherein the processor hardware is configured to execute instructions to:
assign a first one of the multiple data sources as a mandatory data source in the workflow; and
assign a second one of the multiple data sources as an optional data source in the workflow.

6. The computer system of claim 1, wherein the processor hardware is configured to execute instructions to:
identify an outbound process based on the workflow and at least one attribute; and
generate an outbound event in response to identification of the outbound process.

7. The computer system of claim 1, wherein the multiple data sources include at least three different data sources each configured to store different data corresponding to different portions of portion of the distributed workflow integrated application.

8. The computer system of claim 1, wherein:
the data object includes multiple tables;
at least one of the multiple tables is configured to store healthcare patient data; and
at least one of the multiple tables is configured to store healthcare claims data.

9. The computer system of claim 8, wherein the standard data model includes at least one of a pharmacy level rule, a patient identification check rule, a routing rule, a medical rule, a duplicate rule, an eligibility prioritization rule, and a configurable sequencing rule.

10. A method for database playback for distributed workflow integrated applications, the method comprising:
defining a standard data model, the standard data model configured to support a workflow;

obtaining access details for obtaining data from multiple data sources, the multiple data sources each configured to store different data for a portion of a distributed workflow integrated application;

setting up a data modeling engine to connect to the multiple data sources, based on the obtained access details;

preparing a configuration table to return a list of the multiple data sources used in the workflow and an execution order of the multiple data sources;

collecting, by the data modeling engine, data from the multiple data sources; and preparing a data object using the standard data model and the data collected from the multiple data sources;

building, by the data modeling engine, the workflow for the distributed workflow integrated application using a dynamic data source with decision tables; and integrating the data object with the workflow built by the data modeling engine using at least one of an extensible markup language (XML) data structure or a representational state transfer (REST) application programming interface (API).

11. The method of claim 10, wherein the data object is an extensible markup language (XML) data object or a JavaScript object notation (JSON) data object.

12. The method of claim 10, further comprising:
identifying at least one dependency among the multiple data sources; and
defining the execution order of the multiple data sources based on at least one dependency.

13. The method of claim 10, wherein:
obtaining access details for obtaining data from the multiple data sources includes obtaining multiple application programming interfaces each corresponding to a different one of the multiple data sources; and
collecting data from the multiple data sources includes the data modeling engine accessing the multiple data sources via the multiple application programming interfaces.

14. The method of claim 10, further comprising:
assigning a first one of the multiple data sources as a mandatory data source in the workflow; and
assigning a second one of the multiple data sources as an optional data source in the workflow.

15. The method of claim 10, further comprising:
identifying an outbound process based on the workflow and at least one attribute; and
generating an outbound event in response to identification of the outbound process.

16. The method of claim 10, wherein the multiple data sources include at least three different data sources each configured to store different data corresponding to different portions of portion of the distributed workflow integrated application.

17. The method of claim 10, wherein:
the data object includes multiple tables;
at least one of the multiple tables is configured to store healthcare patient data; and
at least one of the multiple tables is configured to store healthcare claims data.

18. The method of claim 17, wherein the standard data model includes at least one of a pharmacy level rule, a patient identification check rule, a routing rule, a medical rule, a duplicate rule, an eligibility prioritization rule, and a configurable sequencing rule.

\* \* \* \* \*